(12) United States Patent
Lin et al.

(10) Patent No.: US 8,611,064 B2
(45) Date of Patent: Dec. 17, 2013

(54) MAGNETIZATION APPARATUS

(75) Inventors: Ray-Lee Lin, Tainan (TW); Tsu-Hua Al, Taoyuan Hsien (TW); Jia-Chi Liu, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 20 days.

(21) Appl. No.: 13/527,977

(22) Filed: Jun. 20, 2012

(65) Prior Publication Data

US 2012/0327548 A1    Dec. 27, 2012

(30) Foreign Application Priority Data

Jun. 24, 2011    (TW) .............................. 100122232 A

(51) Int. Cl.
*H01H 9/00*    (2006.01)

(52) U.S. Cl.
USPC .......................................... 361/143; 361/160

(58) Field of Classification Search
USPC .......................................... 361/139, 144, 160
See application file for complete search history.

(56) References Cited

U.S. PATENT DOCUMENTS 6,232,742 B1 *   5/2001   Wacknov et al. .............. 318/811
2008/0007190 A1 *   1/2008   Kunii et al. .................... 318/141

* cited by examiner

*Primary Examiner* — Danny Nguyen
(74) *Attorney, Agent, or Firm* — Muncy, Geissler, Olds & Lowe, PLLC

(57) ABSTRACT

A magnetization apparatus includes a power supply unit, an energy storage element and a voltage clamp unit. The power supply unit generates at least one exciting signal to excite at least a coil of a magnetic field generating apparatus. The voltage clamp unit has a clamping voltage. The voltage level of the clamp voltage is higher than the voltage level of the exciting signal, and lower than the rated voltage of the energy storage element. When the exciting signal turns to a low voltage level, the voltage clamp unit controls the voltage level of the energy storage element to be less than or equal to the voltage level of the clamp voltage. This configuration with the voltage clamp unit can extend the lifetime of the energy storage element and reduce the energy loss to enhance the efficiency.

12 Claims, 8 Drawing Sheets

MAGNETIZATION APPARATUS

CROSS REFERENCE TO RELATED APPLICATIONS

This Non-provisional application claims priority under 35 U.S.C. §119(a) on Patent Application No(s). 100122232 filed in Taiwan, Republic of China on Jun. 24, 2011, the entire contents of which are hereby incorporated by reference.

BACKGROUND OF THE INVENTION

1. Field of Invention

The present invention relates to a magnetization apparatus and, in particular, to a magnetization apparatus that can extend the lifetime of the energy storage element and reduce the energy loss to enhance the efficiency.

2. Related Art

The targeted therapy is to inject a targeted medicine into a patient body to attack a specific cell (e.g. a tumor cell). However, the injected targeted medicine may be dispersed to every part of the body, so the targeted therapy efficiency is decreased. Besides, the dispersion of the medicine may cause unpredictable side effect, which may bring additional injury to patients. In order to improve the efficiency of targeted therapy, the magnetic guidance control system is introduced to the targeted therapy. The magnetic guidance control system includes a magnetic field generating apparatus for generating a proper magnetic force, which can guide the magnetic targeted medicine to a specific area so as to effectively treat a certain disease.

FIG. 1 is a circuit diagram showing a conventional magnetization apparatus 1, which can control a magnetic field generating apparatus to generate the desired magnetic field for guiding the magnetic particles or magnetic medicine to a specific position so as to effectively treat a certain disease.

The magnetization apparatus 1 includes a DC voltage supply unit 11, an energy storage element 12, an energy release unit 13, three full-bridge conversion units 141-143, and a current feedback unit 15.

The DC voltage supply unit 11 generates at least one exciting signal ES for enabling the coils $T_A$, $T_B$ and $T_C$ to generate magnetic fields to control the magnetic particles or magnetic medicine. The energy storage element 12 is electrically connected with the DC voltage supply unit 11 and stores the energy E generated by demagnetizing the coils $T_A$, $T_B$ and $T_C$. The energy release unit 13 is electrically connected with the DC voltage supply unit 11 and the energy storage element 12 for eliminating the energy E generated by demagnetizing the coils $T_A$, $T_B$ and $T_C$. The full-bridge conversion units 141-143 are electrically connected with the DC voltage supply unit 11, the energy storage element 12 and the energy release unit 13, and respectively connected to the coils $T_A$, $T_B$ and $T_C$. The full-bridge conversion units 141-143 are alternately turned on. That is, the coil of one phase is excited after another coil of a previous phase is demagnetized to eliminate the energy E. In addition, each of the full-bridge conversion units 141-143 includes four switches S1-S4. FIG. 1 only shows the switches S1-S4 of the full-bridge conversion unit 141 connecting to the coil $T_A$. The current feedback unit 15 respectively senses the currents flowing through the coils $T_A$, $T_B$ and $T_C$, and then outputs a control signal DS to control the ON/OFF statuses of the switches S1-S4 of the full-bridge conversion units 141-143, thereby exciting or demagnetizing the coils $T_A$, $T_B$ and $T_C$, respectively. As a result, the magnetic particles or magnetic medicine can be controlled and guided to the specific position.

Taking the coils $T_A$ as an example, however, when the exciting signal ES is in a low voltage level, the control signal DS controls to turn on the switches S2 and S3 and turn off the switches S1 and S4 so as to eliminate the energy E generated by demagnetizing. In this case, the energy E generated by demagnetizing the coil $T_A$ can flow back to the energy storage element 12 and the energy release unit 13 through the switches S2 and S3, so that the terminal voltage of the energy storage element 12 increases and exceeds the rated voltage of the energy storage element 12. This usually shortens the lifetime of the energy storage element 12. In addition, the conventional energy release unit 13 does not have the passive demagnetizing function, so it must be synchronized with the DC voltage supply unit 11. In other words, after the exciting signal ES of one coil is switched to a low voltage level and the energy release unit 13 is simultaneously enabled to absorb the energy E generated by demagnetizing the coil, another coil can then be excited. For example, after the coil $T_A$ is demagnetized and the energy release unit 13 absorbs the energy E generated by demagnetizing the coil $T_A$, the DC voltage supply unit 11 outputs another exciting signal ES to excite another coil $T_B$. This configuration usually results some loss of the energy E at the energy release unit 13 and thus decreases the efficiency of the magnetization apparatus 1.

Therefore, it is an important subject of the present invention to provide a magnetization apparatus that can extend the lifetime of the energy storage element and reduce the energy loss to enhance the efficiency.

SUMMARY OF THE INVENTION

In view of the foregoing subject, an objective of the present invention is to provide a magnetization apparatus that can extend the lifetime of the energy storage element and reduce the energy loss to enhance the efficiency.

To achieve the above objective, the present invention discloses a magnetization apparatus including a power supply unit, an energy storage element and a voltage clamp unit. The power supply unit generates at least one exciting signal to excite at least a coil of a magnetic field generating apparatus. The energy storage element is electrically connected with the power supply unit. The voltage clamp unit is electrically connected with the power supply unit and the energy storage element and has a clamping voltage. The voltage level of the clamp voltage is higher than the voltage level of the exciting signal, and lower than the rated voltage of the energy storage element. When the exciting signal turns to a low voltage level, the voltage clamp unit controls the voltage level of the energy storage element to be less than or equal to the voltage level of the clamp voltage.

In one embodiment, the power supply unit comprises a constant-voltage power supply or a constant-voltage current-limited power supply.

In one embodiment, when the exciting signal turns to the low voltage level, the energy generated by demagnetizing the coil is transferred to the energy storage element.

In one embodiment, when the exciting signal turns to the low voltage level, the voltage clamp unit controls the internal switch thereof according to the voltage level of the energy storage element, thereby controlling the voltage level of the energy storage element to be less than or equal to the voltage level of the clamp voltage.

In one embodiment, the exciting signal comprises a DC signal or a pulse signal.

In one embodiment, the exciting signal comprises an overdrive current signal.

In one embodiment, the over-drive current signal and the exciting signal are in the same phase or opposite phase.

In one embodiment, when the magnetic field generating apparatus has multiple coils, the power supply unit outputs a plurality of exciting signals to excite the coils respectively.

In one embodiment, the exciting signals are partially overlapped.

In one embodiment, the magnetization apparatus further includes at least a full-bridge conversion unit electrically connected with the coil, the power supply unit, the voltage clamp unit and the energy storage element, and the full-bridge conversion unit is disposed corresponding to the coil.

In one embodiment, the magnetization apparatus further includes a control unit electrically connected with the full-bridge conversion unit for controlling an operation of the full-bridge conversion unit so as to enable the exciting signal to exciting the coil or to demagnetizing the coil.

In one embodiment, the magnetization apparatus further includes a current feedback unit for sensing the current of the coil to control an operation of the full-bridge conversion unit so as to enable the exciting signal to exciting the coil or to demagnetizing the coil.

As mentioned above, the magnetization apparatus of the invention is configured with a voltage clamp unit with a clamp voltage, and the voltage level of the clamp voltage is higher than the voltage level of the exciting signal outputted by the power supply unit. Thus, the voltage clamp unit can provide the passive demagnetizing function, which can use the energy generated by demagnetizing one coil to excite another coil. This function can prevent the demagnetizing energy loss at the voltage clamp unit so as to increase the efficiency of the magnetization apparatus. In addition, the voltage level of the clamp voltage is lower than the rated voltage of the energy storage element, and when the exciting signal turns to a low voltage level, the voltage clamp unit controls the voltage level of the energy storage element to be less than or equal to the voltage level of the clamp voltage. Accordingly, the voltage level of the energy storage element can be clamped by the voltage clamp unit, so that the terminal voltages of two terminals of the energy storage element do not exceed the rated voltage. Thus, the magnetization apparatus of the invention can extend the lifetime of the energy storage element.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
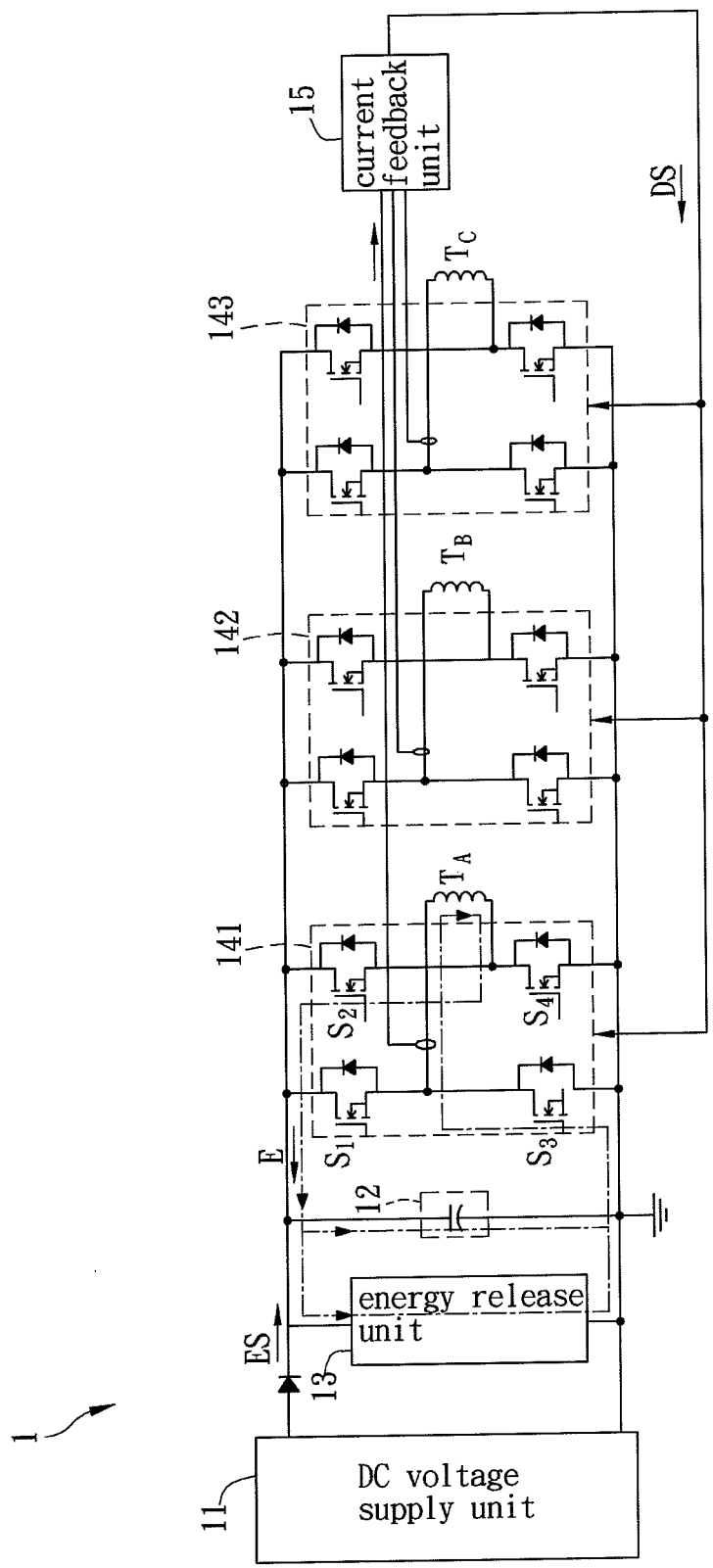
FIG. 1 is a schematic diagram showing a conventional magnetization apparatus.
Figure 2A:
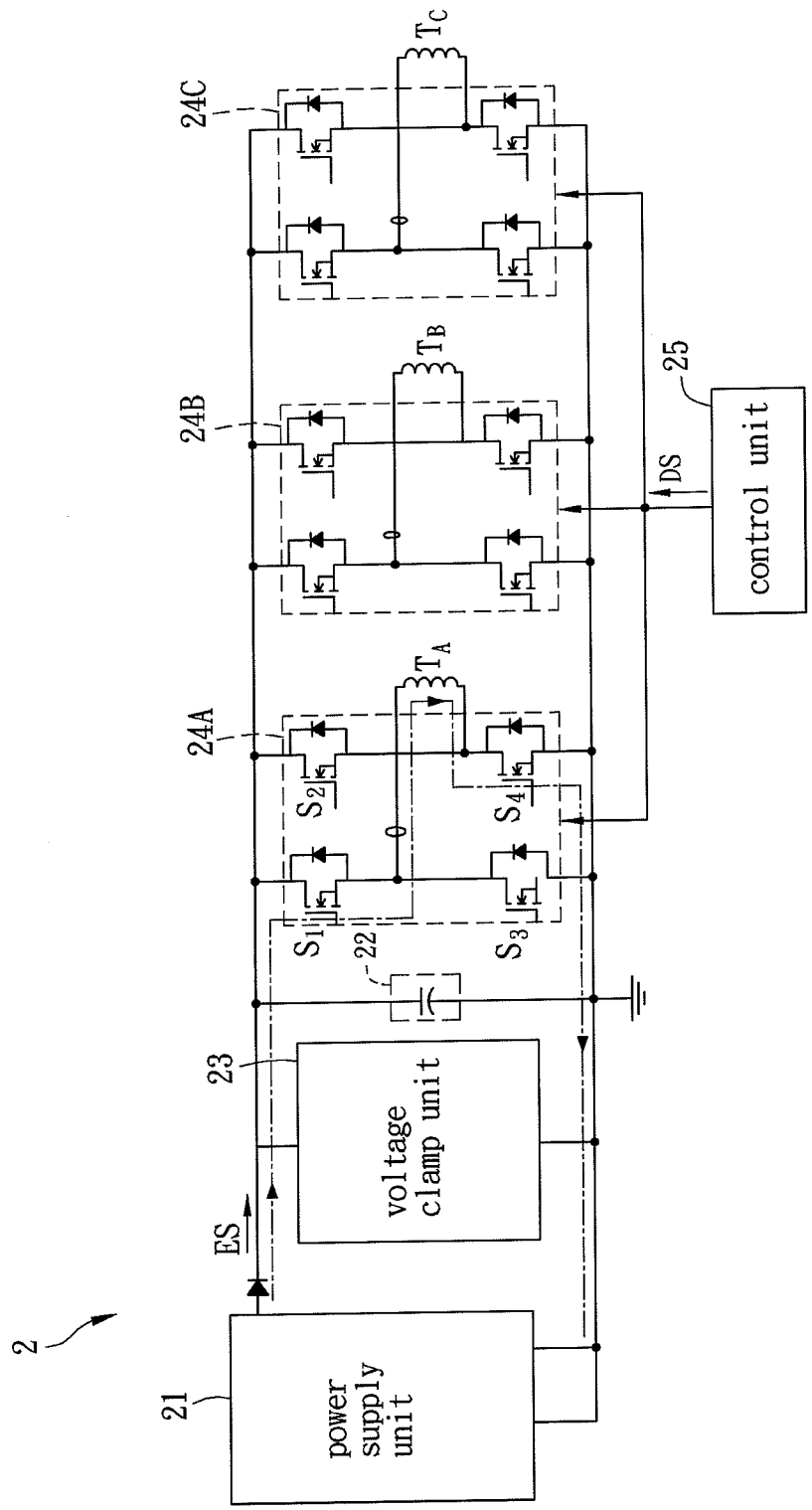
FIGS. 2A and 2B are circuit diagrams of a magnetization apparatus according to a preferred embodiment of the invention.
Figure 2B:
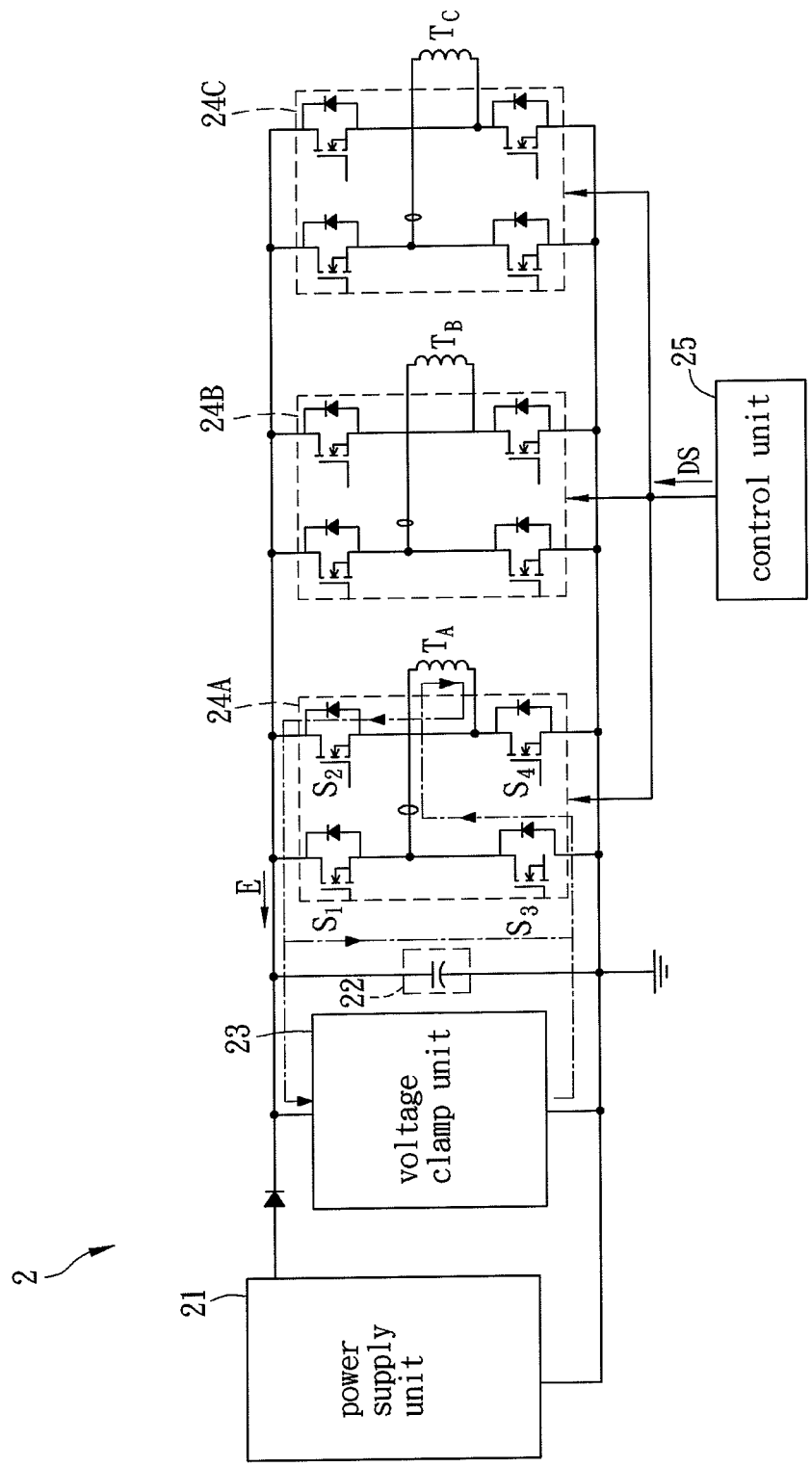

FIGS. 2A and 2B are circuit diagrams of a magnetization apparatus 2 according to a preferred embodiment of the invention. The magnetization apparatus 2 is, for example, applied to the therapeutical applications such as targeted therapy, cardiovascular therapy, medical micro machine guidance, surgical catheter guidance, or the likes. In practice, the magnetization apparatus 2 can control the coil of a magnetic field generating apparatus to generate a proper magnetic field for guiding a magnetic particle, a medical catheter, a medical machine (micro machine), or their combinations. The magnetic particle includes, for example but not limited to, magnetic nano-particle or magnetic nano-medicine.

The magnetization apparatus 2 is cooperated with a magnetic field generating apparatus, which has at least one coil. In this case, the magnetic field generating apparatus has three coils $T_A$, $T_B$ and $T_C$ for example. In addition, the magnetization apparatus 2 includes a power supply unit 21, an energy storage element 22, and a voltage clamp unit 23.

Figure 3A:
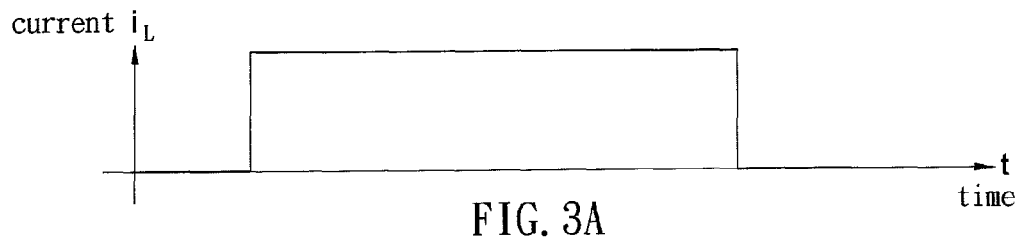
FIGS. 3A to 3F are schematic graphs showing the waveforms of the current signals flowing through the coils.
Figure 3B:
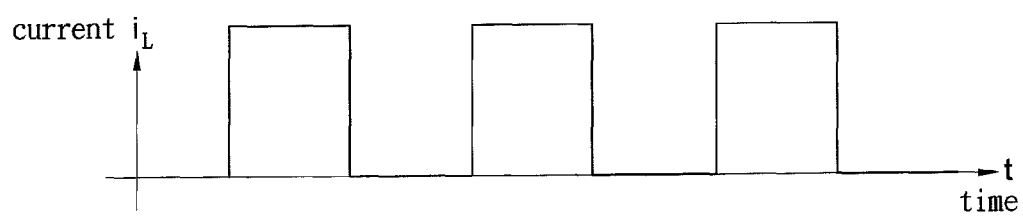

The power supply unit 21 generates at least one exciting signal ES to excite the coils $T_A$, $T_B$ and $T_C$. In practice, the power supply unit 21 outputs a plurality of exciting signals ES for respectively exciting the coils $T_A$, $T_B$ and $T_C$. The exciting signal ES is a current signal, and the current signals flowing through the coils $T_A$, $T_B$ and $T_C$ may include a DC signal (see FIG. 3A) or a pulse signal (see FIG. 3B). When the power supply unit 21 outputs the exciting signals ES, the coils $T_A$, $T_B$ and $T_C$ are controlled to generate magnetic fields for guiding and controlling the movement of a magnetic particle. Besides, when the exciting signals ES are in a low voltage level, the coils $T_A$, $T_B$ and $T_C$ are demagnetized.

The power supply unit 21 includes a constant-voltage power supply or a constant-voltage current-limited power supply. In this case, the power supply unit 21 includes a constant-voltage current-limited power supply for example. When the currents flowing through the coils $T_A$, $T_B$ and $T_C$ rise to reach the maximum current value of the constant-voltage current-limited power supply, the output of the constant-voltage current-limited power supply becomes a constant current. Thus, the magnetic force sensed by the magnetic particle has a linear property, so that the magnetic field generating apparatus can easily control the magnetic particle.

The energy storage element 22 is electrically connected with the power supply unit 21. In this case, the energy storage element 22 is, for example, a capacitor for storing the energy E generated by demagnetizing the coils $T_A$, $T_B$ and $T_C$ as the exciting signals ES are in the low voltage level.

The voltage clamp unit 23 is electrically connected with the power supply unit 21 and the energy storage element 22, and has a clamping voltage $V_C$. The voltage level of the clamp voltage $V_C$ is lower than the rated voltage of the energy storage element 22. In this case, the voltage clamp unit 23 is a constant-voltage DC electronic load, which can control the conductive amount of the internal power switches (e.g. power transistors) according to the inputted voltage level, so that the excess energy can be consumed by the internal loads of the electronic load.

In addition, the voltage level of the clamp voltage $V_C$ is higher than the set voltage level of the power supply unit 21, so that the voltage clamp unit 23 has the passive demagnetizing function. Accordingly, the synchronization of the voltage clamp unit 23 and the power supply unit 21 is not needed. In other words, before one coil is demagnetized, the power supply unit 21 can output another exciting signal ES to excite another coil. For example, the coil $T_B$ can be excited before the coil $T_A$ is demagnetized. Thus, when the exciting signal ES of the coil $T_A$ is in a low voltage level for exciting the coil $T_A$, the demagnetizing energy E can be transferred to the coil $T_B$ to excite it. Accordingly, the energy E is not lost at the voltage clamp unit 23 so as to increase the efficiency of the magnetization apparatus 2.

The magnetization apparatus 2 further includes full-bridge conversion units 24A, 24B and 24C, which are electrically connected with the power supply unit 21, the voltage clamp unit 23, and the energy storage element 22, and are respectively connected to the coils $T_A$, $T_B$ and $T_C$. Each of the full-bridge conversion units 24A, 24B and 24C includes four switches S1-S4. The control unit 25 separately controls the ON/OFF statuses of the switches S1-S4, thereby exciting or demagnetizing the coils $T_A$, $T_B$ and $T_C$, respectively. To be noted, FIGS. 2A and 2B only show the switches S1-S4 connecting to the coil $T_A$.

Moreover, the magnetization apparatus 2 further includes a control unit 25, which is electrically connected with the full-bridge conversion units 24A, 24B and 24C. The control unit 25 can separately control the operations of the full-bridge conversion units 24A, 24B and 24C, so as to enable the exciting signals ES to respectively excite or demagnetize the coils $T_A$, $T_B$ and $T_C$.

The procedures of exciting or demagnetizing the coils $T_A$, $T_B$ and $T_C$ of the magnetization apparatus 2 will be illustrated hereinafter with reference to FIGS. 2A and 2B.

As shown in FIG. 2A, when the control unit 25 outputs a control signal DS to turn on the switch S1 and S4 of the full-bridge conversion unit 24A, the power supply unit 21 outputs the constant-voltage exciting signal ES, which flows through the switch S1, the coil $T_A$ and the switch S4 so as to excite the coil $T_A$. In this case, the coil $T_A$ is excited by the constant voltage. After the excited current of the coil $T_A$ rises and reaches the maximum current value of the power supply unit 21 (e.g. a constant-voltage current-limited power supply), the power supply unit 21 outputs the constant current, which facilitates the control of the magnetic particles. Herein, the control signal DS is a PWM (pulse width modulation) signal.

To be noted, as shown in FIGS. 3C to 3F, when the exciting signal ES is applied to excite the coils $T_A$, $T_B$ and $T_C$, the current signal flowing through the coils $T_A$, $T_B$ and $T_C$ contains an over-drive current signal (see the regions R of FIGS. 3C to 3F). The over-drive current signal can effectively increase the controllability of guiding the magnetic particle. In addition, the over-drive current signal and the exciting signal ES are, for example, in the same phase or out of phase.

Figure 3C:
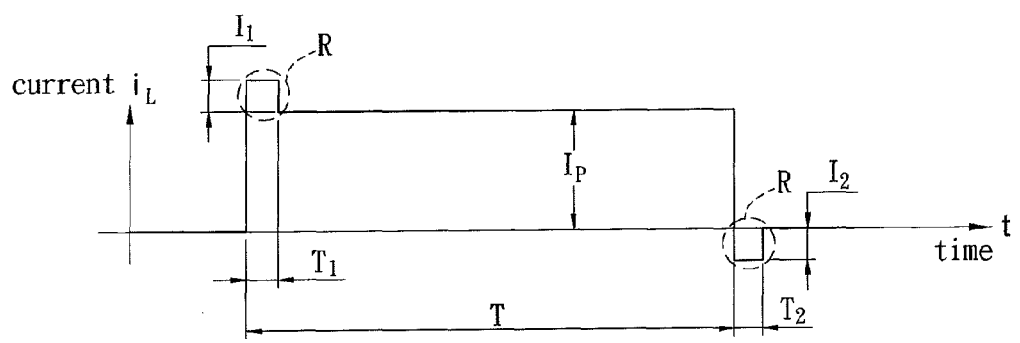
Figure 3D:
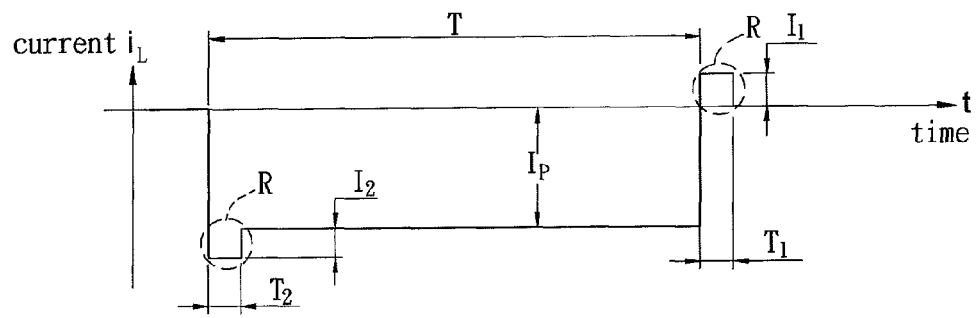
Figure 3E:
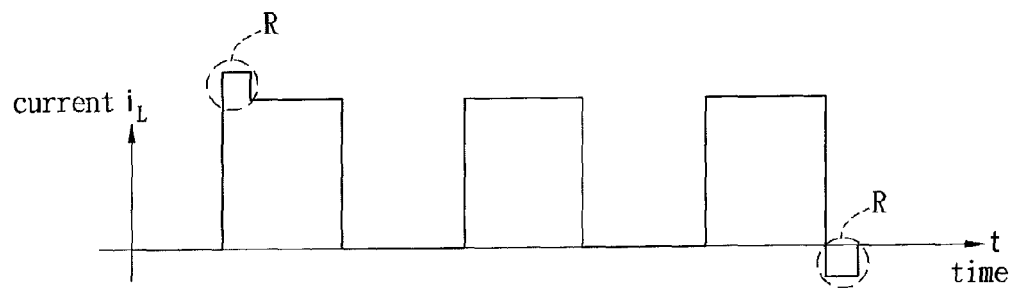
Figure 3F:
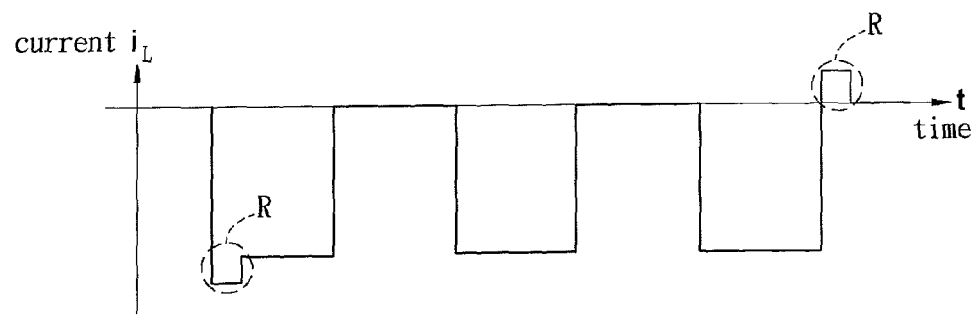

The power supply unit 21 outputs the exciting signal ES with positive or negative current pulse, and also contains the positive over-drive current flowing through the coils $T_A$, $T_B$ and $T_C$ (see FIG. 3E) for instantly decelerating the magnetic particle to stop at a desired position. As shown in FIGS. 3C and 3D, the over-drive current flowing through the coils $T_A$, $T_B$ and $T_C$ is a controllable current signal. Herein, the controllable parts thereof include the positive over-drive current $I_1$, the positive over-drive current time $T_1$, the negative over-drive current $I_2$, the negative over-drive current time $T_2$, the current peak $I_P$, and the excited (conducted) time T. Accordingly, by the above over-drive current method, the user can control the magnetic particle based on the actual needs. For example, the magnetic particle can be controlled to move by overcoming the static frictional force, or to instantly decelerate to stop at a specific position.

Referring to FIG. 2B, when the exciting signal ES is in the low voltage level, the switches S1 and S4 of the full-bridge conversion unit 24A are turned off, and the switches S2 and S3 thereof are turned on, thereby demagnetizing the coil $T_A$ and releasing the energy E to the energy storage element 22 through the switches S2 and S3. The operation of the voltage clamp unit 23 can be controlled according to the voltage level of the energy storage element 22. When the energy storage element 22 is charged by the energy E, and the voltage level of the energy storage element 22 is raised to be equal to the clamp voltage $V_C$ of the voltage clamp unit 23, the internal switches of the voltage clamp unit 23 are controlled to turn on. Thus, the energy E can be released to and absorbed by the voltage clamp unit 23 so as to decrease the voltage of both terminals of the energy storage element 22 to be clamped by the clamp voltage $V_C$. As a result, when the power supply unit 21 outputs the exciting signal ES of a low voltage level, the voltage clamp unit 23 can control the voltage level of the energy storage element 22 to be less than or equal to the voltage level of the clamp voltage $V_C$. Besides, the voltage level of the energy storage element 22 is controlled to be less than the rated voltage so as to extend the lifetime of the energy storage element 22.

Figure 4A:
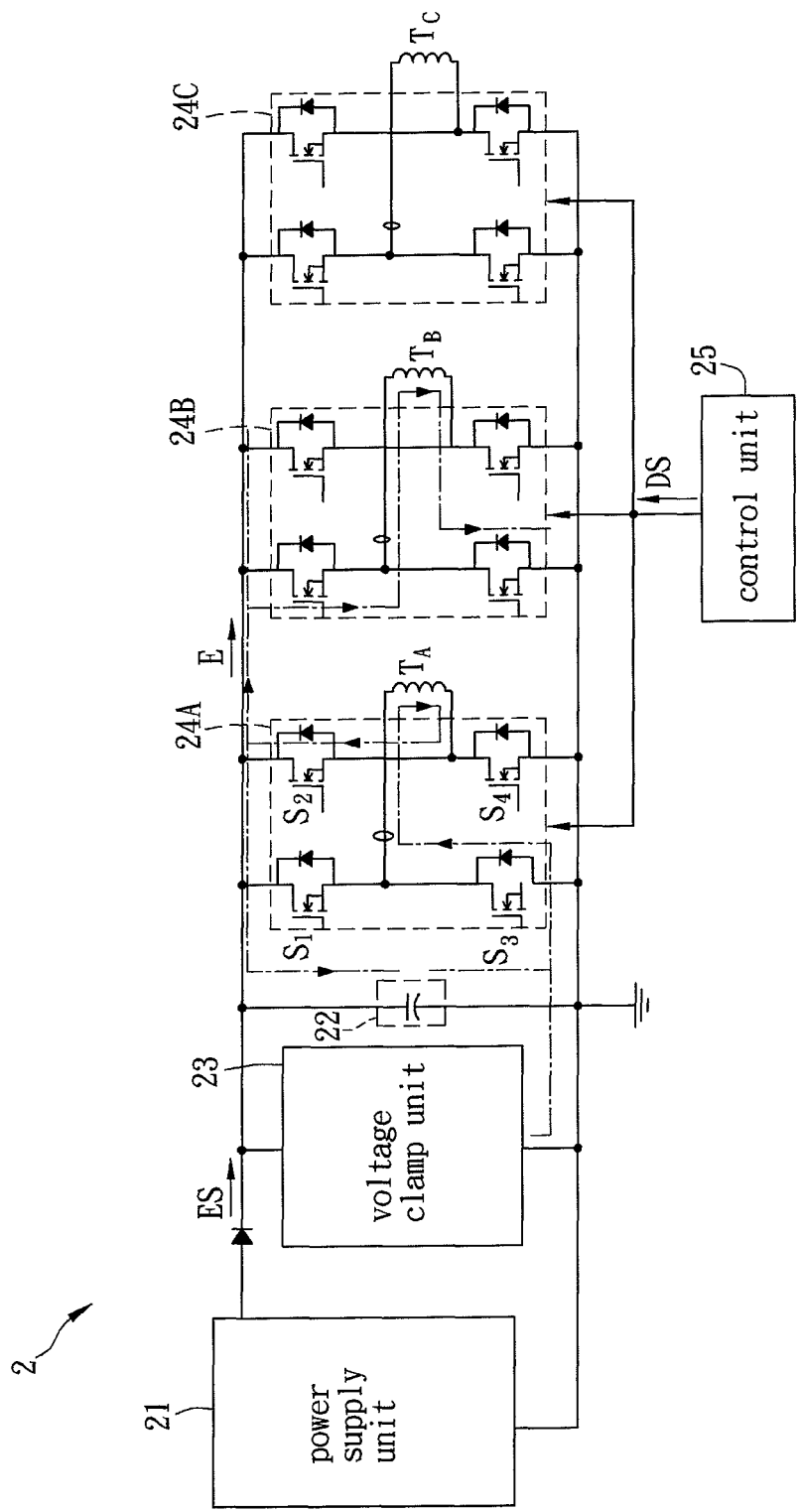
FIG. 4A is a circuit diagram of the magnetization apparatus.
Figure 4B:
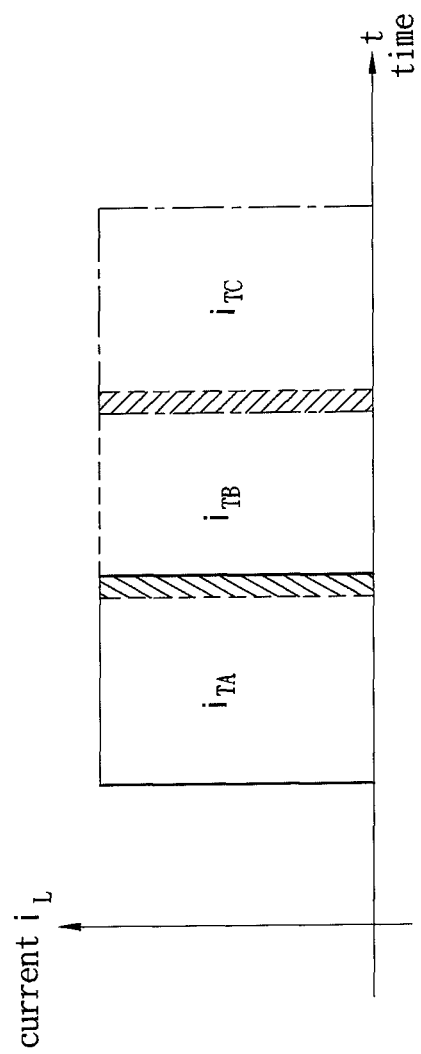
FIG. 4B is a schematic graph showing the waveform of the exciting signal.

With reference to FIGS. 4A and 4B, the power supply unit 21 can output a plurality of exciting signals ES for exciting the coils $T_A$, $T_B$ and $T_C$, respectively. Besides, the driving currents flowing through the coils $T_A$, $T_B$ and $T_C$ are partially overlapped (see the marked stripe region of FIG. 4B), and the overlapping time can be adjusted based on the requirement. In other words, when the coil $T_A$ is excited, it is possible to exciting the coil $T_B$ of another phase simultaneously. After the coil $T_A$ is demagnetized, the demagnetizing energy E is provided to excite the coil $T_B$, so that the coil $T_B$ can be simultaneously excited. Referring to FIG. 4A, the energy E generated by demagnetizing the coil $T_A$ is not consumed on the voltage clamp unit 23, so that the energy loss can be decreased to achieve the desired energy saving effect and increase the efficiency of the magnetization apparatus 2. Similarly, when the coil $T_B$ is excited, it is possible to exciting the coil $T_C$ of another phase simultaneously. After the coil $T_B$ is demagnetized, the demagnetizing energy is provided to excite the coil $T_C$, so that the coil $T_C$ can be simultaneously excited. Accordingly, the magnetization apparatus 2 can control the full-bridge conversion units 24A, 24B and 24C to simultaneously exciting or demagnetizing the coils $T_A$, $T_B$ and $T_C$, respectively.

Figure 5:
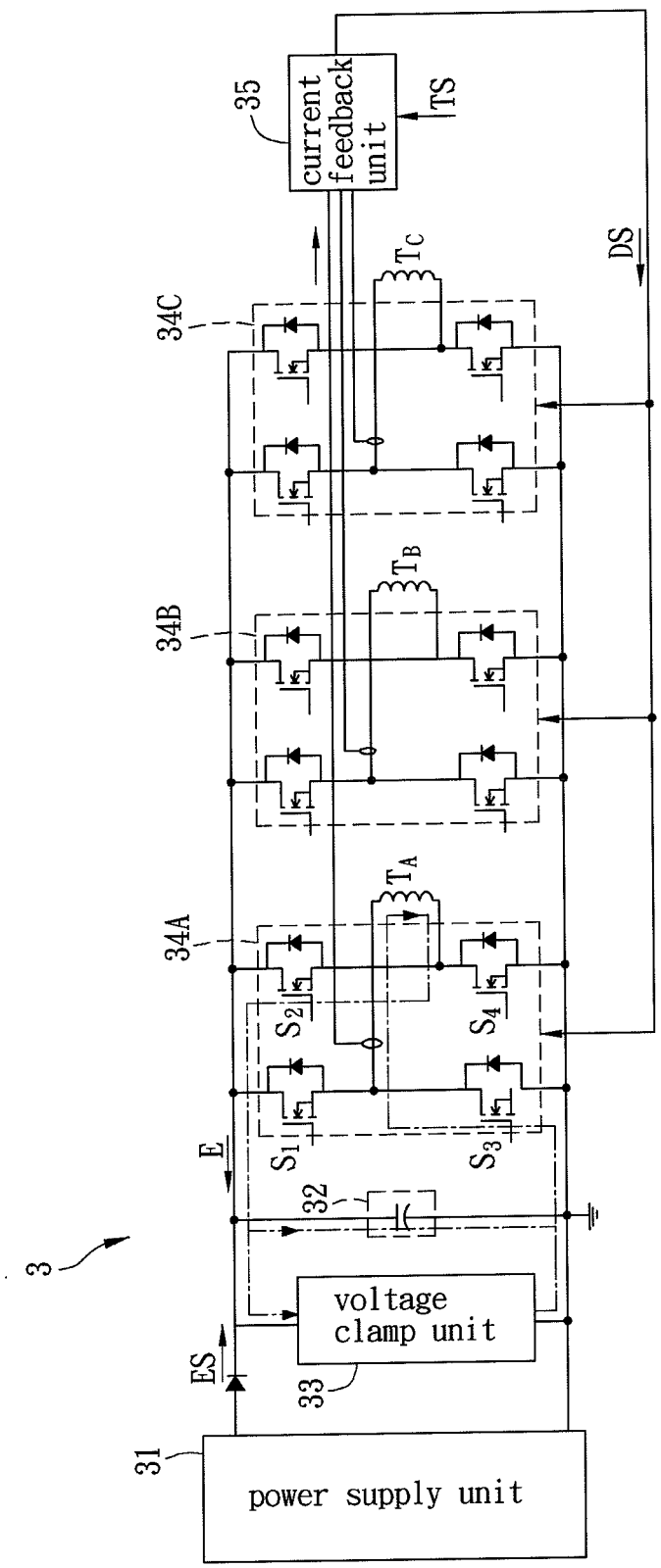
FIG. 5 is a circuit diagram of a magnetization apparatus according to another preferred embodiment of the invention.

FIG. 5 is a circuit diagram of a magnetization apparatus 3 according to another preferred embodiment of the invention.

Referring to FIG. 5, the magnetization apparatus 3 includes a power supply unit 31, an energy storage element 32 and a voltage clamp unit 33. Besides, the magnetization apparatus 3 further includes the full-bridge conversion units 34A, 34B and 34C.

Different from the above-mentioned magnetization apparatus 2, the power supply unit 31 of the magnetization apparatus 3 is a constant-voltage power supply (without current limitation). In addition, the magnetization apparatus 3 further includes a current feedback unit 35 for separately sensing the currents flowing through the coils $T_A$, $T_B$ and $T_C$, so as to control the operations of the full-bridge conversion units 34A, 34B and 34C. By controlling the operations of the full-bridge conversion units 34A, 34B and 34C, it is possible to control the exciting signal ES to excite or demagnetize the coils $T_A$, $T_B$ and $T_C$. The magnetization apparatus 3 detects the currents flowing through the coils $T_A$, $T_B$ and $T_C$ by the current feedback unit 35, and then outputs a voltage signal (not shown). After comparing this voltage signal with a current tracing signal TS, a PWM control signal DS is generated to drive the full-bridge conversion unit 34A, thereby turning on/off the switches S1-S4 of the full-bridge conversion units 34A. Herein, the current tracing signal TS is a pulse signal.

The technical features of other components of the magnetization apparatus 3 can be referred to the same components of the magnetization apparatus 2, so the detailed description thereof is omitted.

In summary, the magnetization apparatus of the invention is configured with a voltage clamp unit with a clamp voltage, and the voltage level of the clamp voltage is higher than the voltage level of the exciting signal outputted by the power supply unit. Thus, the voltage clamp unit can provide the passive demagnetizing function, which can use the energy generated by demagnetizing one coil to excite another coil. This function can prevent the demagnetizing energy loss at the voltage clamp unit so as to increase the efficiency of the magnetization apparatus. In addition, the voltage level of the clamp voltage is lower than the rated voltage of the energy storage element, and when the exciting signal turns to a low voltage level, the voltage clamp unit controls the voltage level of the energy storage element to be less than or equal to the voltage level of the clamp voltage. Accordingly, the voltage level of the energy storage element can be clamped by the voltage clamp unit, so that the terminal voltage of the energy storage element do not exceed the rated voltage. Thus, the magnetization apparatus of the invention can extend the lifetime of the energy storage element.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A magnetization apparatus, which is cooperated with a magnetic field generating apparatus having at least a coil, the magnetization apparatus comprising:
   a power supply unit generating at least an exciting signal to excite the coil;
   an energy storage element electrically connected with the power supply unit; and
   a voltage clamp unit electrically connected with the power supply unit and the energy storage element and having a clamping voltage, wherein the voltage level of the clamp voltage is higher than the voltage level of the exciting signal and lower than the rated voltage of the energy storage element, and when the exciting signal turns to a low voltage level, the voltage clamp unit controls the voltage level of the energy storage element to be less than or equal to the voltage level of the clamp voltage.

2. The magnetization apparatus of claim 1, wherein the power supply unit comprises a constant-voltage power supply or a constant-voltage current-limited power supply.

3. The magnetization apparatus of claim 1, wherein when the exciting signal turns to the low voltage level, the energy generated by demagnetizing the coil is transferred to the energy storage element.

4. The magnetization apparatus of claim 1, wherein when the exciting signal turns to the low voltage level, the voltage clamp unit controls the internal switch thereof according to the voltage level of the energy storage element, thereby controlling the voltage level of the energy storage element to be less than or equal to the voltage level of the clamp voltage.

5. The magnetization apparatus of claim 1, wherein the exciting signal comprises a DC signal or a pulse signal.

6. The magnetization apparatus of claim 1, wherein the exciting signal comprises an over-drive current signal.

7. The magnetization apparatus of claim 6, wherein the over-drive current signal and the exciting signal are in the same phase or opposite phase.

8. The magnetization apparatus of claim 1, wherein when the magnetic field generating apparatus has multiple coils, the power supply unit outputs a plurality of exciting signals to exciting the coils respectively.

9. The magnetization apparatus of claim 8, wherein the exciting signals are partially overlapped.

10. The magnetization apparatus of claim 1, further comprising:
    at least a full-bridge conversion unit electrically connected with the coil, the power supply unit, the voltage clamp unit and the energy storage element, and disposed corresponding to the coil.

11. The magnetization apparatus of claim 10, further comprising:
    a control unit electrically connected with the full-bridge conversion unit for controlling an operation of the full-bridge conversion unit so as to enable the exciting signal to exciting the coil or to demagnetizing the coil.

12. The magnetization apparatus of claim 10, further comprising:
    a current feedback unit for sensing the current of the coil to control an operation of the full-bridge conversion unit so as to enable the exciting signal to exciting the coil or to demagnetizing the coil.

* * * * *